United States Patent [19]

Moser et al.

[11] 4,199,494

[45] Apr. 22, 1980

[54] METAL COMPLEXES OF α-AMINOPHOSPHONIC ACID HALF-ESTERS AND OF α-AMINOPHOSPHINIC ACIDS

[75] Inventors: Paul Moser, Riehen; Jean Rody, Basel, both of Switzerland

[73] Assignee: Ciba-Geigy Corporation, Ardsley, N.Y.

[21] Appl. No.: 862,698

[22] Filed: Dec. 21, 1977

Related U.S. Application Data

[63] Continuation of Ser. No. 682,871, May 3, 1976, abandoned, which is a continuation-in-part of Ser. No. 503,426, Sep. 5, 1974, abandoned.

[30] Foreign Application Priority Data

Sep. 13, 1973 [CH] Switzerland ...................... 13181/73
Jul. 30, 1974 [CH] Switzerland ...................... 10473/74

[51] Int. Cl.$^2$ .......................... C07F 15/04; C08K 5/34
[52] U.S. Cl. .......................... 260/45.75 N; 260/439 R
[58] Field of Search ............ 260/429.9, 429 R, 448 R, 260/429.7, 438.5 R, 439 R, 944, 502.5, 45.75 N, 45.9 NP

[56] References Cited

U.S. PATENT DOCUMENTS

| | | | |
|---|---|---|---|
| 2,635,112 | 4/1953 | Fields | 260/944 |
| 2,794,817 | 6/1957 | Bersworth | 260/438.1 |
| 2,841,611 | 7/1958 | Bersworth | 260/500 |
| 3,036,108 | 5/1962 | Frost | 260/439 R X |
| 3,102,107 | 8/1963 | Soeder | 260/45.75 N |
| 3,160,632 | 12/1964 | Fon Toy | 260/268 |
| 3,316,331 | 4/1967 | Sims | 260/944 |
| 3,332,987 | 7/1967 | Popoff et al. | 260/500 |
| 3,488,368 | 1/1970 | Spivack | 260/429.7 |
| 3,567,768 | 3/1971 | Yu Shen | 260/502.5 |
| 3,767,735 | 10/1973 | Fenyes et al. | 260/946 |
| 3,824,192 | 7/1974 | DiBattista et al. | 252/400 A |

FOREIGN PATENT DOCUMENTS

2122069 11/1971 Fed. Rep. of Germany ...... 260/439 R

OTHER PUBLICATIONS

Jogadic, Chem. Berichte 93, pp. 2308–2313 (1960).

Primary Examiner—Helen M. S. Sneed
Attorney, Agent, or Firm—Vincent J. Cavalieri; Luther A. R. Hall

[57] ABSTRACT

Metal salts of monoalkyl α-aminophosphonates or of α-aminophospinates show a considerable thermostability. Obviously the amino groups are coordinated on the metal atom. These complex salts are soluble in organic solvents and compatible even with non-polar plastics such as polyolefins. They are effective stabilizers against the light-induced deterioration of polymers with an outstanding duration of this activity.

The cation of these salts may be a complex-forming multivalent metal, preferable nickel, cobalt, zinc and aluminum. The amino group may be primary, secondary or tertiary. The complex salts are prepared according conventional processes, for example by conversion of the corresponding alkali phosphonate with a metal halide in organic solution.

14 Claims, No Drawings

METAL COMPLEXES OF α-AMINOPHOSPHONIC ACID HALF-ESTERS AND OF α-AMINOPHOSPHINIC ACIDS

This is a continuation of application Ser. No. 682,871 filed on May 3, 1976, now abandoned which is a continuation-in-part of application Ser. No. 503,426, filed on Sept. 5, 1974, now abandoned.

The invention relates to new organic metal salt complexes, to their manufacture and to their use for stabilising polymers against degradation induced by light. These are compounds of the formula I.

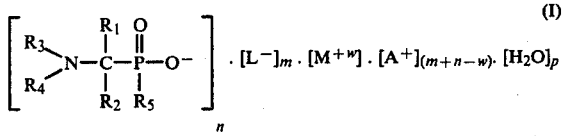

wherein $R_1$ and $R_2$ independently of one another represent hydrogen, alkyl, aralkyl, aryl or aryl or aralkyl which are substituted by chlorine and/or alkyl groups and/or alkoxy groups, or $R_1$ and $R_2$, conjointly with the C atom to which they are linked, form a cycloalkane ring, $R_3$ and $R_4$ independently of one another denote hydrogen, alkyl, alkoxyalkyl, cycloalkyl, aralkyl or aralkyl substituted by chlorine and/or alkyl groups and/or alkoxy groups, and, if one or only one of the substituents $R_1$ and $R_2$ represents an aromatic radical, $R_3$ or $R_4$ can also be aryl or an aryl radical substituted by chlorine and/or alkyl groups and/or alkoxy groups, or $R_3$ and $R_4$, conjointly with the N atom to which they are linked, form a saturated, heterocyclic ring, $R_5$ denotes alkyl, cycloalkyl, aralkyl, aryl, alkoxy, cycloalkoxy, aralkoxy or aryloxy, it being possible for the aromatic radical to be substituted by chlorine and/or alkyl groups and/or alkoxy groups, $L^-$ denotes the monovalent anion of a carboxylic acid, $M^{+w}$ denotes the w-valent cation of a metal from the series of cations $Mg^{+2}$, $Ca^{+2}$, $Sr^{+2}$, $Ba^{+2}$, $Zn^{+2}$, $Cd^{+2}$, $Al^{+3}$, $Sn^{+4}$, $Sn^{+2}$, $VO^{+2}$, $Cr^{+3}$, $Co^{+2}$, $Ni^{+2}$, $MoO_2^{+2}$, $A^+$ denotes the cation of an alkali metal, n denotes an integer from 1 to 4, m denotes an integer from 1 to 3 or zero, w designates an integer from 2 to 4, and p denotes a value from zero to 2.

A preferred embodiment of the invention are the above compounds of formula I wherein $R_1$ and $R_2$ independently of one another represent hydrogen, alkyl, aralkyl, aryl or aryl or aralkyl which are substituted by chlorine and/or alkyl groups and/or alkoxy groups, or $R_1$ and $R_2$, conjointly with the C atom to which they are linked, form a cycloalkane ring, $R_3$ and $R_4$ independently of one another denote hydrogen, alkyl, alkoxyalkyl, cycloalkyl, aralkyl or aralkyl substituted by chlorine and/or alkyl groups and/or alkoxy groups, and, if none or only one of the substituents $R_1$ and $R_2$ represents an aromatic radical, $R_3$ or $R_4$ can also be aryl or an aryl radical substituted by chlorine and/or alkyl groups and/or alkoxy groups, or $R_3$ and $R_4$, conjointly with the N atom to which they are linked, form a saturated, heterocyclic ring, $R_5$ denotes alkyl, cycloalkyl, aralkyl, aryl, alkoxy, cycloalkoxy, aralkoxy or aryloxy, it being possible for the aromatic radical to be substituted by chlorine and/or alkyl groups and/or alkoxy groups, $L^-$ denotes the monovalent anion of a carboxylic acid, $M^{+w}$ denotes the w-valent cation of a metal from the series of cations $Mg^{+2}$, $Ca^{+2}$, $Sr^{+2}$, $Ba^{+2}$, $Zn^{+2}$, $Cd^{+2}$, $Al^{+3}$, $Sn^{+4}$, $Sn^{+2}$, $VO^{+2}$, $Cr^{+3}$, $Co^{+2}$, $Ni^{+2}$ or $MoO_2^{+2}$, $A^+$ denotes the cation of an alkali metal, n denotes an integer from 1 to 4, m denotes an integer from 1 to 3 or zero, w denotes an integer from 2 to 4, and p denotes a value from zero to 2, provided that, if $M^{+w}$ is $Zn^{+2}$, m is zero and (m+n−w) is zero, $R_3$ and $R_4$ are not both hydrogen.

Of the metal salts described in the immediately preceding paragraph, those are particularly preferred wherein $M^{+w}$ is the w-valent cation from the series of cations $Mg^{+2}$, $Ca^{+2}$, $Sr^{+2}$, $Ba^{+2}$, $Cd^{+2}$, $Al^{+3}$, $Sn^{+4}$, $Sn^{+2}$, $VO^{+2}$, $Cr^{+3}$, $Vo^{+2}$, $Ni^{+2}$, or $MoO_{Co}^{+2}$ if $R_3$ and $R_4$ are both hydrogen.

If $R_1$, $R_2$; $R_3$, $R_4$ or $R_5$ denotes alkyl, it can be linear or branched alkyl groups, for example methyl, ethyl, propyl, isopropyl, n-butyl, n-hexyl, n-octyl, 2-ethylhexyl, n-dodecyl or n-octadecyl. If $R_3$ and $R_4$ denote alkoxyalkyl, it can be, for example, 2-methoxyethyl or 3-methoxypropyl. If Cr substituents denote aralkyl or substituted aralkyl, it can be, for example, benzyl, 4-methylbenzyl, 4-isopropylbenzyl, 3-chlorobenzyl, 4-methoxybenzyl, 2,4-dichlorobenzyl, 2-chloro-4-methylbenzyl, 1-naphthylmethyl or 2-naphthylmethyl, phenylethyl or 2-naphthylethyl. In the meaning of aryl or substituted aryl, the same substituents can be, for example, phenyl, diphenylyl, naphthyl, 4-methylphenyl, 3-chlorophenyl, 3,4-dichlorophenyl, 4-methoxynaphthyl-1, 4-butoxyphenyl, 3-chloro-4-methylphenyl or 3-ethoxyphenyl. If $R_1$ and $R_2$, conjointly with the C atom to which they are linked, form a cycloalkane ring, it can be, for example, a cyclopentane, cyclohexane or 4-methylcyclohexane ring.

If $R_3$, $R_4$ or $R_5$ denote cycloalkyl, it can be, for example, cyclopentyl, cyclohexyl or 3-methylcyclohexyl. If $R_3$ and $R_4$, conjointly with the N atom to which they are linked, form a saturated, heterocyclic ring, it can be, for example, a pyrrolidine, methylpyrrolidine, dimethylpyrrolidine, piperidine, morpholine, N-methylpiperazine or N-ethylpiperazine ring. If $R_5$ denotes an alkoxy or cycloalkoxy radical, it can be, for example, a methoxy, ethoxy, isopropoxy, butoxy, hexoxy, 2-ethylhexoxy or cyclohexoxy radical. $R_5$, in the meaning of aralkoxy or substituted aralkoxy, can be, for example, a benzoxy, 4-chlorobenzoxy, 2,4-dichlorobenzoxy, 3-methylbenzoxy or 2-phenylethoxy radical. $R_5$, in the meaning of aryloxy or substituted aryloxy, can be, for example, a phenoxy, p-tolyloxy, 4-chlorophenoxy, β-naphthoxy, 3-methoxyphenoxy or 3-chloro-4-methylphenoxy group.

According to the definition, $L^-$ is the monovalent anion of a carboxylic acid. Possible carboxylic acids are both aliphatic or cycloaliphatic and aromatic or aralphatic carboxylic acids. They can be monocarboxylic acids or partial esters of polycarboxylic acids. The carboxylic acids can be unsaturated and can carry substituents such as, for example, ether or ester groups. Examples of suitable carboxylic acids are: acetic acid, glycollic acid, diglycollic acid monohexyl ester, lactic acid, 2-ethylcaproic acid, maleic acid monobutyl ester, thiodiglycollic acid monododecyl ester, lauric acid, oleic acid, stearic acid, cyclohexanecarboxylic acid, hexahydrophthalic acid monooctyl ester, phthalic acid monobutyl ester, benzoic acid, 4-hydroxy-3,5-di-tert. butylbenzoic acid, salicyclic acid, salicylic acid propyl ether, phenylacetic acid or 2-naphthyl propionic acid. $A^+$, in the meaning of alkali metal cation, can be $Na^+$, $K^+$, $Li^+$, $Rb^+$ or $Cs^+$. If m is zero, this means that the aminophosphonate or aminophosphinate anion is the only anion in the complex. The index $(m+n-w)$ for the cation $[A^+]$ arises from the requirement of ionic neutrality. This index can be zero, and in this case $[M^{+w}]$ is the only cation in the complex. The presence of $[L^+]$ and therefore optional, while both the other ions are essential.

The water content expressed in formula I by $[H_2O]_p$ can generally be attributed to a content of water in the metal salts used as the starting material. Depending on the conditions of isolation and drying, this water can occur partly as a ligand of the central atom $M^{+w}$, but can also partly be held as water of crystallisation in the end product. The coefficient p can therefore have both the value of an integer and of a fractional number, within the limits indicated.

Preferred compounds are those of the formula I wherein $R_1$ and $R_2$ independently of one another represent hydrogen, alkyl having 1 to 12 C atoms, aralkyl having 7 to 11 C atoms or aryl having 6 to 12 C atoms, it being possible for the aromatic ring to be monosubstituted or disubstituted by chlorine and/or methyl and/or alkoxy groups having 1 to 8 C atoms, or $R_1$ and $R_2$, conjointly with the C atom to which they are linked, form a cyclopentane or cyclohexane ring, $R_3$ and $R_4$ independently of one another denote hydrogen, alkyl having 1 to 12 C atoms, cycloalkyl having 5 or 6 C atoms, or an aralkyl radical which has 7 to 13 C atoms and which can be monosubstituted or disubstituted by chlorine and/or methyl groups and/or alkoxy groups having 1 to 8 C atoms, or, if none or only one of the substituents $R_1$ and $R_2$ represents an aroamtic radical, $R_3$ or $R_4$ can also denote an aryl radical which can be monosubstituted or disubstituted by chlorine and/or alkyl groups having 1 to 4 C atoms and/or alkoxy groups having 1 to 8 C atoms, or $R_3$ and $R_4$, conjointly with the N atom to which they are linked, form a heterocyclic ring of the pyrrolidine, piperidine, piperazine or morpholine series, $R_5$ represents alkyl having 1 to 8 C atoms, cycloalkyl having 5 or 6 C atoms, aralkyl having 7 to 13 C atoms, or aryl having 6 to 12 C atoms, it being possible for the aromatic ring to be monosubstituted or disubstituted by chlorine and/or methyl groups and/or alkoxy groups having 1 to 8 C atoms, or $R_5$ denotes an alkoxy radical having 1 to 8 C atoms, the cyclohexoxy radical, the benzoxy radical, the phenoxy radical or a phenoxy radical which is monosubstituted or disubstituted by chlorine or by methyl groups, $L^-$ denotes the monovalent anion of an aliphatic carboxylic acid having 1 to 18 C atoms, or of cyclohexanecarboxylic acid or of an araliphatic carboxylic acid having 8 to 12 C atoms, or of an aromatic carboxylic acid which has 7 to 11 C atoms and which can be substituted by 1 or 2 alkyl radicals having 1 to 4 C atoms, and/or by a hydroxyl group, $M^{+w}$ represents a cation from the series of cations $Zn^{+2}$, $Al^{+3}$, $Co^{+2}$ or $Ni^{+2}$, and $A^+$ denotes the cation of an alkali metal, n denotes an integer from 1 to 3, m denotes the number 1 or 2 or zero, p denotes a value from 0 to 2, and w denotes the number 2 or 3.

Of the meanings listed here for $M^{+w}$, that of $Ni^{+2}$ is particularly important, because the nickel complexes of the formula I exhibit a particularly good stabilising action.

Preferred compounds are, furthermore, those of the formula I, wherein $R_1$ and $R_2$ independently of one another denote hydrogen, alkyl having 1 to 8 C atoms, benzyl, phenyl or a phenyl radical substituted by $CH_3$ or $CH_3O$—, or wherein $R_1$ and $R_2$, conjointly with the C atom to which they are linked, form a cyclohexane ring, $R_3$ and $R_4$ independently of one another denote hydrogen, alkyl having 1 to 8 C atoms, cyclohexyl or an aralkyl radical which has 7 to 11 C atoms and which can be monosubstituted by methyl, chlorine or alkoxy groups having 1 to 4 C atoms, or, if none or only one of the substituents $R_1$ and $R_2$ represents an aromatic radical, $R_3$ or $R_4$ can also denote a phenyl radical which can be monosubstituted or disubstituted by chlorine and/or alkyl having 1 to 4 C atoms and/or alkoxy groups having 1 to 4 C atoms, or $R_3$ and $R_4$, conjointly with the N atom to which they are linked, form a pyrrolidine, piperidine or morpholine ring, $R_5$ denotes alkyl having 1 to 8 C atoms, cyclohexyl, aralkyl having 7 to 11 C atoms, and aryl radical which has 6 to 10 C atoms and which can be monosubstituted by Cl, $CH_3$ or $CH_3O$, an alkoxy radical having 1 to 4 C atoms, the benzoxy radical, the phenoxy radical, a chlorophenoxy radical or a tolyloxy radical, $L^-$ represents the anion of acetic acid, 2-ethylcaproic acid, lauric acid, oleic acid, stearic acid, phenylacetic acid, benzoic acid, 4-hydroxy-3,5-di-tert.butylbenzoic acid or naphthoic acid, $M^{+w}$ represents a cation from the series $Zn^{+2}$, $Al^{+3}$, $Co^{+2}$ or $Ni^{+2}$, but preferably $Ni^{+2}$, and $A^+$ denotes the cation of an alkali metal, n denotes an integer from 1 to 3, m denotes the number 1 or 2 or zero, w denotes the number 2 or 3, and p denotes a value from 0 to 2.

Particularly preferred compounds are those of the formula I wherein $R_1$ denotes hydrogen, alkyl having 1 to 6 C atoms, phenyl or 4-methoxyphenyl, $R_2$ denotes hydrogen or methyl, $R_3$ denotes hydrogen, alkyl having 2 to 8 C atoms, cyclohexyl or benzyl, $R_4$ denotes hydrogen, alkyl having 2 to 8 C atoms, cyclohexyl, phenyl, 4-methoxyphenyl or 2-methoxy-5-tert.butylphenyl, or $R_3$ and $R_4$, conjointly with the nitrogen atom, denote a piperidine or morpholine radical, $R_5$ denotes alkyl having 1 to 4 C atoms, phenyl, 4-tolyl, 4-methoxyphenyl or an alkoxy radical having 1 to 4 C atoms, $L^-$ denotes the anion of acetic acid, ethylcaproic acid, lauric acid, stearic acid or 4-hydroxy-3,5-di-tert.butylbenzoic acid, $M^{+w}$ denotes the cation $Ni^{+2}$, $A^+$ denotes the cation $Na^+$ or $K^+$, n denotes the number 1 or 2, m denotes the number 1 or 2 or zero, w denotes the number 2, and p denotes a value from 0 to 2.

Another particularly preferred embodiment of the invention are those compounds of the formula I wherein $R_3$ and $R_4$ are not both hydrogen. Of these secondary and tertiary amino compounds, those are especially preferred wherein $M^{+w}$ is a cation selected from $Zn^{+2}$, $Al^{+3}$, $Co^{+2}$, and $Ni^{+2}$.

The secondary and tertiary amino $Al^{+3}$, $Co^{+2}$ and $Ni^{+2}$ salts, and most especially the secondary and tertiary amino $Ni^{+2}$ salts, are considered to represent a partially advantageous group of compounds of the invention.

Examples of compounds of the formula I are:

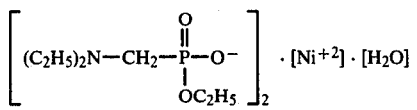
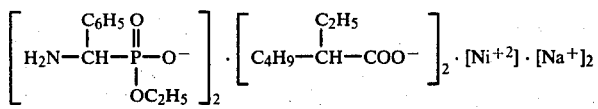
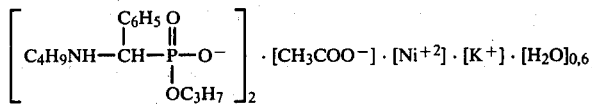
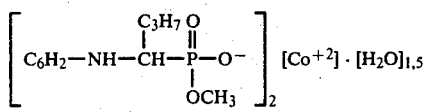
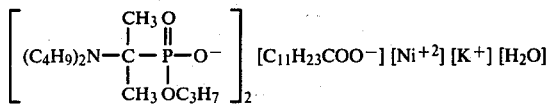
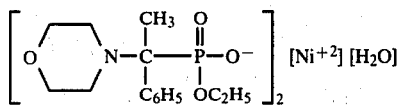
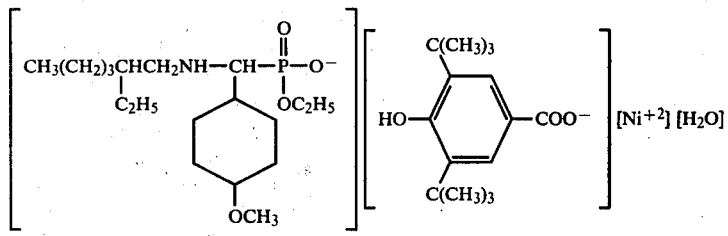
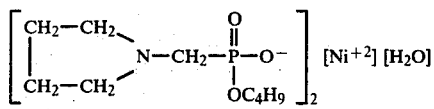
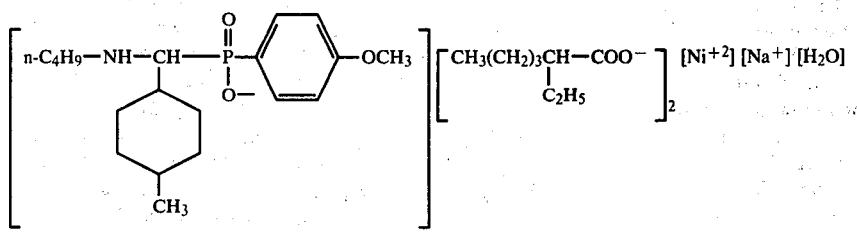
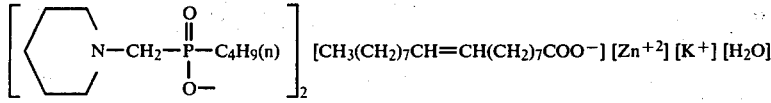
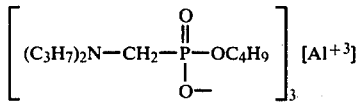
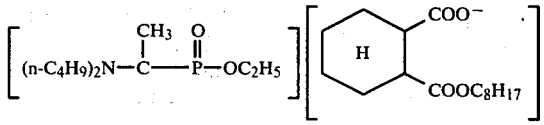

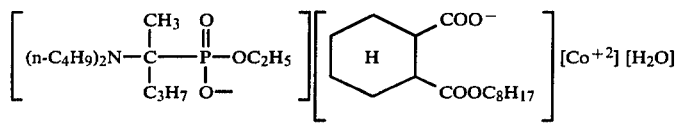

These new compounds of the formula I can be prepared quite generally by reacting, in solution, an alkali metal salt of the formula II

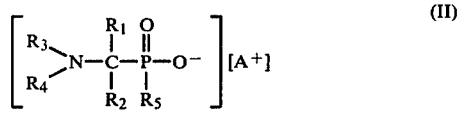

with a metal salt of the formula III $$[M^{+n}] [X^-]_w \cdot [H_2O]_q \qquad (III)$$

wherein q represents any desired value from 0 to 6, X represents a monovalent anion and the symbols $R_1$–$R_5$, A, M and w have the same meaning as in formula I.

The alkali metal salts of the formula II can be employed as such or can be directly prepared in the reaction medium by neutralising a corresponding α-aminophosphonic acid half-ester or an α-aminophosphinic acid with an alkali metal compound. A suitable alkali metal compound for this purpose is, for example, the hydroxide or alcoholate or, if the acid is sufficiently acidic, also the carbonate or bicarbonate.

The reaction of II with III can be carried out in the stoichiometric molar ratio w:1, but it can also be carried out in a molar ratio deviating from this, for example (w−1):1 or (w+1):1. By varying the molar ratio it is possible to regulate, within certain limits, the values n and m and thus the composition of the complex of the formula I. The known half-esters of the α-aminophosphonic acids are appropriately obtained by partial hydrolysis of the corresponding diesters. Literature examples carrying out such partial hydrolyses are described in Houben-Weyl "Methoden der organischen Chemie" ("Methods of Organic Chemistry"), volume 12/1, pages 410 et seq. A general method of preparing the diesters has been described by E. K. Fields in the Journal of the American Chemical Society 74 (1952), 1528. In this, phosphorous acid diesters are reacted with a carbonyl compound and an amine. If phosphonous acid monoesters are used here instead of the phosphorous acid diesters, the α-aminophosphinic acid esters are obtained (in this context see M. J. Kabachnick, T. Y. Medved, Chem.Abstr. 50, 219 (1956), and A. N. Pudovik, Chem. Abstr. 49, 3050 (1955)), which can be saponified by alkaline or acid hydrolysis to give the free acids.

Examples of suitable metal salts of the formula III are nickel chloride dihydrate, nickel bromide, the Ni salt of 2-ethylcaproic acid, cobalt (II) stearate, zinc acetate and aluminium trichloride.

If the phosphonic acid half-esters or phosphinic acids on which the salts of formula II are based are sufficiently acidic, it is possible, for the preparation of compounds of the formula I in which especially m is equal to zero and n=w, to simplify the process described above by directly reacting these acids with one equivalent of a metal salt, the anion of which is sufficiently basic. A carbonate, for example nickel carbonate, is suitable for this purpose. It is also possible to proceed by reacting, with the acids on which formula II is base, the metal oxides concerned, such as, for example, zinc oxide, the metal hydroxides, such as, for example, cadmium hydroxide, or metal alkoxides, such as, for example, aluminium isopropylate, instead of the metal salts of the formula III.

Examples of suitable solvents for this reaction are water, alcohols (especially methanol, ethanol and isopropanol), ethylene glycol monoalkyl ethers, dioxane, tetrahydrofurane, acetonitrile and mixtures thereof. The reaction is carried out by heating the reaction solutions for several hours at about 30° to 130° C. In certain cases it is merely necessary to mix the components thoroughly in one of the solvents mentioned. As these preparative processes are generally equilibrium reactions, the compounds of the formula I which are formed are often produced as mixtures, the compositions of which are distinguished by different values for n, m and p. This is especially the case if a molar ratio of the reaction components II and III is chosen which deviates from the equivalent ratio w:1. The isolation of the complexes of the formula I depends on their solubility and on the solubility, in the solvent used, of the alkali metal salt $[A^+]$ $[X^-]$ formed in the reaction. If the complex is insoluble in the solvent, it can be isolated by filtration. If the alkali metal salt is insoluble, it is filtered off and the complex is obtained by evaporating the solution. If both components are soluble, the solution is evaporated and the complex is isolated by extraction with a solvent of low polarity, in which the alkali metal salt is insoluble. Examples of suitable solvents for this purpose are diethyl ether, methylene chloride, chloroform, benzene or toluene.

If the anion $[X^-]$ has a sufficiently strong co-ordinating power, it can incorporate itself in the metal complex as a ligand $[L^-]$. *The alkali metal cation $[A+]$* can then form a constituent of the complex as an ion of opposite charge. In these cases an alkali metal salt is not isolated when working up as described above, because it has then become a constituent of the soluble complex.

The products which are obtained, in some cases not in a pure form, but as mixtures of complexes of the formula I, in these isolation operations, are just as suitable for stabilising polymers as the unitary complexes.

Another process for preparing compounds of the formula I in which m is zero and which do not contain an alkali metal cation, consists of reacting, at temperatures of above 100° C., the esters of the formula IV

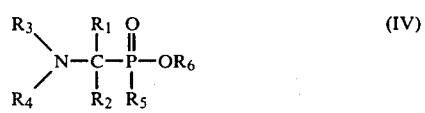

wherein $R_6$ denotes an alkyl radical having 1 to 4 C atoms, and the remaining symbols have the same meaning as in formula I, with a metal halide $MHal_w$. In this case the ester radical splits off in the form of alkyl halide $R_6Hal$, with he formation of a complex metal salt of the formula I. In this case Hal denotes chlorine, bromine or iodine. Examples of metal halides which are suitable for this reaction, are $ZnCl_2$, $CdI_2$, $NiCl_2$, $CoBr_2$ and $AlCl_3$.

In the form of individual compounds or of mixtures, the compounds of the formula I are outstanding stabilisers for polymers against degradation thereof induced by light. In addition, they also act in the polymers as dyestuff receptors and thus increase their dyeability by means of chelatable dyestuffs. It is already known to use organic salts or complexes of metals such as nickel and divalent cobalt as light protection agents for polymers, especially for polyolefines.

For example, nickel complexes of thio-bisphenols, nickel salts of substituted benzoic acids, particularly hydroxybenzoic acids, or nickel sats of phosphonic acids are known.

In the new compounds of the formula I, the organic ligands are linked to the metal both in the manner of a salt and co-ordinatively. This lends to a high thermal and hydrolytic stability in the complexes, so that, for example, on incorporating such stabilisers in hot plastic melts, discolorations do not occur and on weathering the stabiliser is not washed out of the polymer protected by it. The decisive advantage of the compounds of the formula I compared with the known metal-containing stabilisers mentioned is their surprisingly long duration of effectiveness. The latter can be determined by measuring the time over which a stabilised polymer retains certain mechanical properties under conditions of ageing. The "protection factor" is obtained by comparing this time with the correspondingly measured time for a non-stabilised polymer. This protection factor which can be achieved with the new compounds is 20 to 30% higher than that of the known metal stabilisers mentioned above.

Polymeric substrates which should be mentioned as being protected by the metal complexes of the formula I against degradation, are above all poly-α-olefines, such as polyethylene, crosslinked polyethylene, polypropylene, polyisobutylene, polymethylbutene-1, polymethylpentene-1, polybutene-1, polyisoprene and polybutadiene; and also polystyrene and copolymers thereof, such as, for example, polyacrylonitrile-styrene copolymers of polycrylonitrile-butadien-styrene copolymers; copolymers of olefines, such as ethylene-propylene copolymers, propylene-butene-1 copolymers and terpolymers of ethylene and propylene with a diene, such as, for example, hexadiene, dicyclopentadien or ethylenenorbornene; mixtures of the abovementioned homopolymers, such as, for example, mixtures of polypropylene and polyethylene, polypropylene and polybutene-1, and polypropylene and polyisobutylene. Polypropylene and mixtures thereof and the copolymers which contain propylene units, are preferred.

The compounds of the formula I are incorporated into the substrates in a concentration of 0.01 to 5% by weight, calculated on the material to be stabilised. Preferably, 0.05 to 1.5% by weight, particularly preferentially 0.1 to 0.8% by weight, of the compounds, calculated on the material to be stabilised, are incorporated into the latter.

The incorporation can be carried out after polymerisation, for example by mixing at least one of the compounds of the formula I and optionally further additives into the melt by the methods which are customary in technology, before or during shaping, or by applying the dissolved or dispersed compounds onto the polymers, if appropriate with subsequent evaporation of the solvent.

The compounds of the formula I can also be incorporated into the polymer to be stabilised in the form of a masterbatch containing the metal stabiliser, for example in a concentration of 2.5 to 25% by weight, In the case of crosslinked polyethylene, the compounds are added before crosslinking. The following should be mentioned as further additives which can be employed together with the stabilisers which can be used in accordance with the invention:

1. Antioxidants 1.1 Simple 2,6-dialkylphenols, such as, for example, 2,6-di-tert.butyl-4-methylphenol, 2-tert.butyl-4,6-dimethylphenol, 2,6-di-tert.butyl-4-methoxymethylphenol and 2,6-dioctadecyl-4-methylphenol.

1.2 Derivatives of alkylated hydroquinones, such as, for example, 2,5-di-tert.butyl-hydroquinone, 2,5-di-tert.amylhydroquinone, 2,6-di-tert.butyl-hydroquinone, 2,5-di-tert.butyl-4-hydroxy-anisole, 3,5-di-tert.butyl-4-hydroxy-anisole, tris-(3,5-di-tert.butyl-4-hydroxyphenyl) phosphite, 3,5-di-tert.-butyl-4-hydroxyphenyl stearate and bis-(3,5-di-tert.butyl-4-hydroxyphenyl) adipate.

1.3 Hydroxylated thiodiphenyl ethers, such as, for example 2,2'-thio-bis-(6-tert.butyl-4-methylphenol), 2,2'-thio-bis-(4-octylphenol), 4,4'-thio-bis-(6-tert.butyl-3- methylphenol), 4,4'-thio-bis-(3,6-di-sec.amylphenol), 4,4'-thio-bis-(6-tert.butyl-2-methylphenol) and 4,4'-bis-(2,6-dimethyl-4-hydroxyphenyl) disulphide.

1.4 Alkylidene-bisphenols, such as, for example, 2,2'-methylene-bis-(6-tert.butyl-4-methylphenol),2,2'-methylene-bis-(6-tert.butyl-4-ethylphenol), 4,4'-methylene-bis-(6-tert.-butyl-2-methylphenol), 4,4'-methylene-bis-(2,6-di-tert.butylphenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)butene, 1,1-bis-(5-tert.butyl-4-hydroxy-2-methylphenyl)-butane, 2,2-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.butyl-4-hydroxy-2-methylphenyl)-pentane and ethylene glycol bis-[3,3-bis-(3'-tert.butyl-4'-hydroxyphenyl)-butyrate].

1.5 O-, N- and S-benzyl compounds, such as, for example, 3,5,3',5'-tetra-tert.butyl-4,4'-dihydroxydibenzyl ether, 4-hydroxy-3,5-dimethylbenzyl-mercapto cetic acid octadecyl ester, tri-(3,5-di-tert.butyl-4-hydroxybenzyl)-amino and bis-(4-tert.butyl-3-hydroxy-2,6-dimethylbenzyl)dithiol terephthalate.

1.6 Hydroxybenzylated malonic esters, such as, for example 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert.butyl-4-hydroxybenzyl)-malonic acid didodecylmercaptoethyl ester and 2,2-bis-(3,5-di-tert.butyl-4-hydroxybenzyl)-malonic acid di-[4-(1,1,3,3-tetramethylbutyl)-phenyl] ester.

1.7 Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8 s-Triazine compounds, such as, for example, 2,4-bis-octylmercapto-6-(3,5-di-tert.butyl-4-hydroxy-anilino)-s-triazine, 2-octylmercapto-4,6-bis-(3,5-di-tert.butyl-4-hydroxy-anilino)-s-triazine, 2-octylmercapto- 4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9 Amides of β-(3,5-di-tert.butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-(3,5-di-tert.butyl-4-hydroxyphenyl-propionyl)-hexamethylenediamine.

1.10 Esters of β-(3,5-di-tert.butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, tris-hydroxyethylisocyanurate and 4-hydroxymethyl-1-phospha-2,6,7-trioxabicyclo[2,2,2]octane.

1.11 Esters of β-(5-tert.butyl-4-hydroxy-3-methylphenyl)propionic acid with monohydric or polyhydric alcohols such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, trishydroxyethylisocyanurate and 4-hydroxymethyl-1-phospha-2,6,7-trioxabicyclo[2,2,2]octane.

1.12 Esters of 3,5-di-tert.butyl-4-hydroxyphenylacetic acid with monohydric or polyhydric alcohols such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, tris-hydroxyethylisocyanurate and 4-hydroxymethyl-1-phospha-2,6,7-trioxabicyclo[2,2,2-octane.

1,13 Acylaminophenols, such as, for example, N-(3,5-ditert.butyl-4-hydroxyphenyl)-stearic acid amide and N,N'-di-(3,5-di-tert.butyl-4-hydroxyphenyl)-thio-bis-acetamide.

1.14 Benzylphosphonate, such as, for example, 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.15 Aminoaryl derivatives, such as for example, phenyl- 1-naphthylamine, phenyl-2-naphthylamine, N,N'-diphenyl-p-phenylenediamine, N,N'-di-1-naphthyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminobenzyl, and polymerised 2,2,4-trimethyl-1,2-dihydroquinoline.

2. UV absorbers and light stabilisers 2.1. 2-(2'-Hydroxyphenyl)-benztriazoles, such as, for example, the 5'-methyl-, 3',5'-di-tert.butyl-, 5'-tert.butyl-, 5'-(1,1,3,3-tetramethylbutyl)-, 5-chloro-3',5'-di-tert-.butyl-, 5-chloro-3'-tert.butyl-5'-methyl, 3'-sec.butyl-5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.amyl-, 3'-methyl-5'-carbomethoxyethyl- and 5-chloro-3',5'-di-tert.-amyl-derivative.

2.2. 2,4-Bis-(2'-hydroxyphenyl)-6-alkyl-s-triazines, such as, for example, the 6-ethyl-, 6-heptadecyl- or 6-undecylderivative.

2.3. 2-Hydroxy-benzophenones, such as, for example, the 4-hydroxy-, 4-methoxy-, 4-octoxy-,4-decyloxy, 4-dodecyloxy-, 4-benzyloxy-, 4,2',4'-trihydroxy- or 2'-hydroxy-4,4'-dimethoxyderivative.

2.4. 1,3-Bis-(2'-hydroxybenzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids, such as, for example, phenyl salicylate, octylphenyl salicylate, dibenzoylresorcinol, bis-(4-tert.-butylbenzoyl)-resorcinol, benzoylresorcinol and 3,5-di-tert.-butyl-4-hydroxybenzoic acid 2,4-di-tert.butyl-phenyl ester or octadecyl ester or 2-methyl-4,6-di-tert.butyl-phenyl ester.

2.6. Acrylates, such as, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester and N-(β-carbomethoxy-vinyl)-2-methyl-indoline.

2.7 Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl) sebacate and 3-n-octyl-7,7,9,9-tetramethyl-1,3,8-triazaspiro[4,5]decane-2,4-dione.

2.8. Oxalic acid diamides, such as, for example, 4,4'-dioctyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)oxalamide, 2-ethoxy-5-tert.butyl-2'-ethyl-oxanilide and its mixture with 2-ethoxy-2'-ethyl-5,4'-di-tert.butyl-oxanilide and mixtures of ortho- and para-methoxy- as well as of o- and p-ethoxy-disubstituted oxanilides.

5. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-di-isodecyloxy-2,4,8,10-tetraoxa-3,9-diphosphaspiro[5,5]-undecane and tri-(4-hydroxy-3,5-di-tert.butylphenyl) phosphite.

4. Compounds which destroy peroxide, such as, for example, esters of β-thiodipropionic acid, for example the lauryl, stearyl, myristyl or tridecyl esters, salts of 2-mercaptobenzimidazole, for example the Zn salt, and diphenylthiourea.

5. Basic co-stabilisers, such as, for example, melamine, benzoguanamine, polyvinylpyrrolidone, dicyandiamide, triallylcyanurate, urea derivatives, hydrazine derivatives, amines, polyamides, polyurethanes, and alkali metal salts and alkaline earth metal salts of higher fatty acids, for example Ca stearate, Zn stearate, Mg stearate, Na ricinoleate or K palmitate.

6. Nucleating agents, such as, for example, 4-tert. butyl-benzoic acid, adipic acid and diphenylacetic acid.

7. Other additives, such as, for example, plasticisers, lubricants, emulsifiers, fillers, carbon black, asbestos, kaolin, talc, glass fibres, pigments, flameproofing agents and antistatic agents.

The following examples provide a further illustration of the preparation and use of the compounds of the formula I. Parts here denote parts by weight and percentages (%) denote percentages by weight.

EXAMPLES 1 to 8

(In this context compare Table I)

0.1 mol of the α-aminophosphonic acid half-ester listed in column 2 of Table I is dissolved in 350 ml of absolute ethanol and is converted into the sodium salt by neutralisation with an approx. 1.5 normal ethanolic solution of 0.1 mol of sodium ethylate. The procedure is now according to one of the three methods designated in column 3, by adding 0.05 mol of the following nickel salts, in the form of ethanolic solutions, to the solution of the sodium salt at 25° C.:

Nickel chloride dihydrate, 5% strength solution (method Ia), nickel acetate tetrahydrate, 10% strength solution (method Ib), or nickel 2-ethylhexanoate, 10% strength solution (method Ic).

The mixture is then heated at reflux temperature for 30 minutes. If method Ia is used, the sodium chloride which separates out is filtered off. The filtrate from this, or the solutions obtained in accordance with methods Ib and Ic, are evaporated to dryness. If operating according to method Ia or Ib, the residue is extracted, after drying for 5 hours at 60° C. and under a pressure of 11 mm Hg, with the solvent mentioned in column 4. After being evaporated to dryness, the extract, is, if necessary, submitted to the additional purification described in column 5. The residues from evaporation, obtained with and without additional extraction, and those obtained by method Ic, are dried for 15 hours at the temperature indicated in column 6 under a pressure of 11 mm Hg. These instructions give the nickel complexes listed in column 7, the properties of which are described in columns 8 to 11.

Table I

| 1 Example No. | 2 Aminophosphonic acid half-ester used | 3 Method | 4 Extracting agent | 5 Additional purification | 6 Drying | 7 End product: Ni(II) complex of composition: | 8 % content P | 9 % content Ni | 10 Soluble in: (h) at the boiling point (c) at room temperature | 11 Colour |
|---|---|---|---|---|---|---|---|---|---|---|
| 1 | $CH_2N(C_2H_5)_2$<br>$O=P-OH$<br>$OC_2H_5$ | Ia | $C_6H_6$ | — | 60° C. | $X_2Ni \cdot 1H_2O$<br>X=O-ethyl-di-ethylaminome-thylphosphonate | 13.3 | 12.4 | Ethanol, (c), chloroform (c), toluene (c), ligroin (h) | Yellow-green |
| 2 | $CH_2N(C_2H_5)_2$<br>$O=P-OH$<br>$OC_4H_9(n)$ | Ia | $C_6H_6$ | Extraction with ether | 60° C. | $X_2Ni \cdot 1H_2O$<br>X=O-n-butyl-di-ethylaminome-thylphosphonate | 12.1 | 11.2 | Ethanol (c), chloroform (c), toluene (c), ligroin (h) | Yellow-green |
| 3 | $C_6H_5-CHNH_2$<br>$O=P-OH$<br>$OC_2H_5$ | Ia | — | — | 80° C. | $X_2L_2NiNa_2$<br>X=O-ethyl-α-aminobenzyl-phosphonate<br>L=2-ethylhexanoate | 7.3 | 7.2 | Ethanol (c) chloroform (c) toluene (c) | Light green |
| 4 | $C_6H_5-CH-NHC_4H_9(n)$<br>$O=P-OH$<br>$OC_2H_5$ | Ib | $CH_2Cl_2$ | — | 80° C. | $X_2LNiNa \cdot \tfrac{1}{2}H_2O$<br>X=O-ethyl-α(n-butylamino)-benzyl phosphonate<br>L=acetate | 9.1 | 8.15 | Ethanol (c), chloroform (c), toluene (c), ligroin (h) | Light green |
| 5 | $CH_3O-C_6H_4-CHNHCH_2C_6H_5$<br>$O=P-OH$<br>$OC_2H_5$ | Ib | $CHCl_3$ | Extraction with benzene separating off $H_2O$ by azeotropic distillation | 80° C. | Mixture: $X_2Ni$ and $X_2LNiNa$<br>X=O-ethyl-α benzylamino-p-methoxyben-zylphosphonate<br>L=acetate | 8.0 | 7.7 | Ethanol (c) chloroform (c) toluene (c) ligroin (h) | Light green |
| 6 | $C_6H_5-CHNHC_6H_5$<br>$O=P-OH$<br>$OC_2H_5$ | Ia | $CH_2Cl_2$ | — | 70° C. | $X_2Ni$<br>X=O-ethyl-α-anilino-benzyl-phosphonate | 9.6 | 9.25 | Ethanol (c) chloroform (c) toluene (c) | Yellow green |
| 7 | $C_6H_5-CH-NH-C_6H_3(OCH_3)(C(CH_3)_3)$<br>$O=P-OH$<br>$OC_2H_5$ | Ia | $C_6H_6$ | — | 80° C. | $X_2Ni$<br>X=O-ethyl-α(2-methoxy-5-tert.-butyl-anilino)-ben-zylphosphonate | 7.3 | 7.2 | Ethanol (c), chloroform (c), hexane (h), ether (c) | Yellow green |

Table I-continued

| 1 Example No. | 2 Aminophosphonic acid half-ester used | 3 Method | 4 Extracting agent | 5 Additional purification | 6 Drying | 7 End product: Ni(II) complex of composition: | 8 % content P | 9 % content Ni | 10 Soluble in: (h) at the boiling point (c) at room temperature | 11 Colour |
|---|---|---|---|---|---|---|---|---|---|---|
| 8 | CH$_3$<br>\|<br>C$_6$H$_5$C—NHC$_4$H$_9$(n)<br>\|<br>O=P—OH<br>\|<br>OC$_2$H$_5$ | Ib | CHCl$_3$ | — | 80° C. | X$_2$LNiNa . ½H$_2$O<br>X=O-ethyl-α-n-butylamino-α'-methyl-benzyl-phosphonate<br>L=acetate | 8.8 | 7.8 | Ethanol (c), chloroform (c), toluene (c), ligroin (h) | Light green |

EXAMPLES 9 to 13

(In this context compare Table II)

0.1 mol of the aminophosphonic acid half-esters or aminophosphinic acids listed in column 2 of Table II are dissolved in the solvent and quantity thereof specified in column 3. If water is used, this solution is converted into the sodium salt by adding 0.1 mol of sodium hydroxide as a 10-normal aqueous liquor. If ethanol is used, 0.1 mol of sodium ethylate as a 1.5-normal ethanolic solution is used for this purpose. A solution of 0.05 mol of the nickel salt mentioned in column 4 in 80 ml of the solvent of column 3 is then added dropwise at 25° C. If the nickel salt of the aminophosphonic acid is not immediately precipitated, the mixture is heated at reflux temperature for 45 minutes. The precipitate formed is filtered off, washed with the solvent mentioned in column 3 and dried for 15 hours at 80° C. and under a pressure of 11 mm Hg. In Example 13 an additional purification operation is carried out at this point: the product is extracted with chloroform, the extract is evaporated to dryness, the residue is recrystallised from ethanol/chloroform (1:1) and the precipitate obtained is dried for 15 hours at 80° C. and under a pressure of 11 mm Hg. These instructions give the nickel compounds listed in column 5, the properties of which are described in columns 6 to 9.

Table II

| 1 Example No. | 2 α-Aminophosphonic acid half-ester or α-amono-phosphine acid | 3 Solvent (quantity in ml) | 4 Ni(II) salt | 5 End product: Ni(II)- | 6 % content P | 7 % content Ni | 8 Solubility: soluble in: (h) at the boiling point, (c) at room temperature | 9 Colour |
|---|---|---|---|---|---|---|---|---|
| 9 | C$_6$H$_{13}$(n)—CHNHC$_4$H$_9$(n)<br>\|<br>O=P—OH<br>\|<br>OC$_2$H$_5$ | Water (3000) | NiCl$_2$ . 6H$_2$O | Bis-(O-ethyl-α-n-butyl-amino heptane-phospho-nate) | 10.0 | 9.4 | Sparingly soluble in organic solvents | Blue-green |
| 10 | C$_6$H$_5$—CH—NH$_2$<br>\|<br>O=P—OH<br>\|<br>OC$_2$H$_5$ | Water (500) | NiCl$_2$ . 6H$_2$O | Bis-(O-ethyl-α-amino-methane-phosphonate)-dihydrate | 12.1 | 11.0 | Sparingly soluble in organic solvents | Light blue |
| 11 | C$_6$H$_5$CHNHCH$_2$CH(CH$_2$)$_3$CH$_3$<br>\|            \|<br>O=P—OH    C$_2$H$_5$<br>\|<br>OC$_2$H$_5$ | Water (170) | NiCl$_2$ . 6H$_2$O | Bis-(O-ethyl-α-2-ethyl-hexyl-amino-benzyl-phosphonate) mono-hydrate | 8.5 | 8.2 | Ethanol (c), chloroform (c), toluene (c), hexane (c) | Light green |
| 12 | C$_6$H$_5$CH—NHC$_4$H$_9$(n)<br>\|<br>O=P—OH<br>\|<br>C$_6$H$_5$ | Ethanol (500) | Ni-acetate . 4H$_2$O | Bis-(α-n-butylamino-benzyl-phenylphosphi-nate) | 9.4 | 10.2 | Sparingly soluble in organic solvents | Light green |
| 13 | C$_6$H$_5$CHNH—⟨⟩—OCH$_3$<br>\|<br>O=P—OH<br>\|<br>C$_6$H$_5$ | Water (600) | Ni-acetate . 4H$_2$O | Bis-(α-p-anisidino-benzylphenyl-phos-phinate) dihydrate | 7.9 | 7.4 | Ethanol (c), chloroform (c) toluene (h) | Beige yellow |

EXAMPLE 14

A solution of 13.6 g (0.05 mol) of 0-ethyl-α-n-butylaminobenzylphosphonic acid and 12.5 g (0.05 mol) of 4-hydroxy-3,5-di-tert.butylbenzoic acid in 300 ml of ethanol is neutralised with 0.1 mol of sodium ethylate (approx. 1.5 molar in ethanol). A solution of 6.48 g (0.05 mol) of nickel chloride in 3,000 ml of methanol is then added at 30° C. and the suspension thus formed is evaporated to dryness. The residue is extracted with benzene, the solvent is evaporated and the extract is dried for 15 hours at 80° C. under a pressure of 11 mm Hg. A light green product of the composition XLNi (X=O-ethyl-α-n-butylaminobenzylphosphonate, L=4-hydroxy-3,5-di-tert.butylbenzoate) is obtained in this way, and is readily soluble in ethanol, toluene and ligroin at room temperature. Its phosphorus content is 5.1% and its nickel content is 9.6%.

EXAMPLE 15

30.3 g (0.1 mol) of α-(n-butylamino)benzyl-phenyl-phosphinic acid

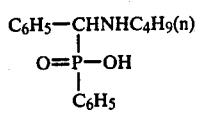

are dissolved in 400 ml of absolute ethanol and neutralised with an approx. 1.5 molar ethanolic solution of 0.1 mol of sodium ethylate. 34.5 g (0.1 mol) of nickel(II) bis (2-ethylhexanoate) are additionally dissolved in this solution and the mixture is heated at reflux temperature for 30 minutes. The solvent is then evaporated and the residue is dried for 15 hours at 80° C. under a pressure of 11 mm Hg. These instructions give a light green product of the composition XLNi (X=α-(n-butylamino)benzyl-phenylphosphinate; L=2-ethylhexanoate), which contains 4.2% of phosphorus and 9.0% of nickel and is readily soluble in ethanol, chloroform, toluene and hexane at room temperature.

EXAMPLES 16 to 20

In the preparation of these nickel complexes listed in Table III, method Ia is used, as in Examples 1–8, with the single difference that, in the case of Examples 17, 19 and 20, the α-aminophosphonic acid half-ester or α-aminophosphinic acid is employed in the form of the potassium salt and the neutralisation with sodium ethylate is therefore superfluous.

The potassium salt of the compound according to Example 20 is obtained by saponifying the ethyl ester of N,N-diethylaminomethane-phenyl-phosphinic acid with an equimolecular quantity of alcoholic potassium hydroxide solution. The ethyl ester itself is prepared by reacting benzenephosphonous acid monoethyl ester with equimolecular quantities of diethylamine and paraformaldehyde, analogously to the method described by E. K. Fields for the preparation of α-aminophosphonic acid esters from dialkyl phosphites, carbonyl compounds and secondary amines (J. Am. Chem. Soc 74, 1530 (1952)).

Table III

| Example No. | Aminophosphonic acid half-ester or amino-phosphinic acid X= | Extracting agent | Additional purification | Drying temperature | End product: Ni(II) complex of composition: | % content P | % content Ni | Soluble in: (h) at the boiling point (c) at room temperature | Colour |
|---|---|---|---|---|---|---|---|---|---|
| 16 | CH₂—N(C₄H₉.n)₂ / O=P—O⁻ / OC₂H₅ | CH₂Cl₂ | — | 60° C. | H₂Ni.1H₂O X=O-ethyl-di-n-butylamino-methenephosphonate | 10.9 | 9.65 | Ether (c) Benzene (c) Ligroin (h) | Yellow-green (wax) |
| 17 | CH₂—N(piperidine) / O=P—O⁻ / OC₂H₅ | Hexane | — | 50° C. | X₂Ni.1H₂O X=O-ethyl-α-piperidine-methenephosphonate | 12.7 | 12.7 | Chloroform (c) Ether (c) Hexane (c) | Light green |
| 18 | CH₂—N(pyrrolidine) / O=P—O⁻ / OC₂H₅ | Recrystallised from CH₃CN | Recrystallisation from acetonitrile followed by extention with ethanol | 80° C. | X₂Ni.1H₂O X=O-ethyl-α-pyrrolidino-methanephosphonate | 13.4 | 12.4 | Ethanol (c) Methylene chloride (c) Toluene (c) | Light green |
| 19 | CH₂—N(morpholine) / O=P—O⁻ / OC₂H₅ | Not extracted | — | 80° C. | X₂Ni.1H₂O X=O-ethyl-α-morpholino-methanephosphonate | 12.6 | 11.9 | Ethanol (h) Methylene chloride (c) Toluene (c) | Yellow-green |
| 20 | CH₂—N(C₂H₅)₂ / O=P—O⁻ / C₆H₅ | CH₂Cl₂ | — | 80° C. | X₂Ni.1H₂O X=N,N-diethyl-aminomethane-phenylphosphinate | 12.0 | 11.1 | Ethanol (c) Chloroform (c) Benzene (c) Ether (c) | Yellow |

EXAMPLES 21 to 23

In the preparation of these cobalt(II) complexes listed in Table IV, the process used is the same as in the case of the corresponding nickel complexes, Examples 1, 17 and 19. The metal salt is added here in the form of a 15% strength ethanolic solution of anhydrous cobalt(II) chloride.

Table IV

| Example No. | aminophosphonic acid half-ester X= | Extracting agent | Additional purification | Drying-temperature | End product: Co(II) complex of composition: | % content P | % content NI | Soluble in: (h) at the boiling point (c) at room temperature | Colour |
|---|---|---|---|---|---|---|---|---|---|
| 21 | $\text{CH}_2-\text{N}(\text{C}_2\text{H}_5)_2$<br>$\mid$<br>$\text{O}=\text{P}-\text{O}^{\ominus}$<br>$\mid$<br>$\text{OC}_2\text{H}_5$ | $\text{CH}_2\text{Cl}_2$ | Recrystallisation from acetonitrile | 80° C. | $\text{X}_2\text{Co} \cdot \tfrac{1}{2}\text{H}_2\text{O}$<br>X=O-ethyl-diethyl-aminomethane-phosphate | 13.5 | 14.4 | Ethanol (c) Chloroform (c) Toluene (c) | Lilac |
| 22 | $\text{CH}_2-\text{N}\langle\text{piperidino}\rangle$<br>$\mid$<br>$\text{O}=\text{P}-\text{O}^{\ominus}$<br>$\mid$<br>$\text{OC}_2\text{H}_5$ | Ether | — | 60° C. | $\text{X}_2\text{Co}$<br>X=O-ethyl-α-piperidino-methanephosphonate | 12.4 | 12.3 | Ethanol (c) Methylene chloride (c) Toluene (c) | Cobalt blue |
| 23 | $\text{CH}_2-\text{N}\langle\text{morpholino}\rangle\text{O}$<br>$\mid$<br>$\text{O}=\text{P}-\text{O}^{\ominus}$<br>$\mid$<br>$\text{OC}_2\text{H}_5$ | $\text{CH}_2\text{Cl}_2$ | — | 60° C. | $\text{X}_2\text{Co} \cdot \text{H}_2\text{O}$<br>H=O-ethyl-α-morpholino-methane-phosphonate | 12.4 | 11.7 | Ethanol (c) Methylene chloride (c) Toluene (c) | Cobalt blue |

EXAMPLE 24

27.1 g (0.1 mol) of O-ethyl-α-butylamine-benzylphosphonic acid are suspended in 400 ml of water and are converted into the sodium salt with 0.1 mol of sodium hydroxide in the form of a 10-normal aqueous solution. 0.05 mol of a 10% strength solution of cobalt chloride hexahydrate are added dropwise, at 25° C., to the resulting clear solution. The suspension thus formed is stirred for a further hour and the precipitate is filtered off and washed with water. It is then dried for 16 hours at 80° C. and under a pressure of 11 mm Hg. A lilac-coloured product of the composition $\text{CoX}_2$ (X=O-ethyl-α-n-butylamino-benzylphosphonate) is obtained in this way, and is sparingly soluble in organic solvents, but is soluble in polyethylene wax. Its phosphorus content is 9.8% and its cobalt content is 9.6%.

EXAMPLE 25

If 32.7 g (0.1 mol) of O-ethyl-α-(2-ethylhexylamino)-benzyl-phosphonic acid are used as the starting material and the process is otherwise as in Example 24, a violet product of the composition $\text{CoX}_2 \cdot 1/2\text{H}_2\text{O}$ (X=O-ethyl-α-(2-ethylhexylamino)-benzylphosphonate) is obtained, which is readily soluble in toluene at room temperature and in hot ligroin. Its phosphorus content is 8.5% and its cobalt content is 8.3%.

EXAMPLE 26

32.7 g (0.1 mol) of O-ethyl-α-(2-ethylhexylamino)-benzylphosphonic acid are suspended in 500 ml of water and are converted into the sodium salt with 0.1 mol of a 10-normal aqueous solution of sodium hydroxide. 0.05 mol of a 15% strength aqueous solution of zinc chloride is now added dropwise slowly, at 40° C., to the resulting clear solution. An emulsion is thus formed, which is extracted once with 150 ml of ether for ½ hour at 30° C. The ether phase is separated off and evaporated to dryness. The extract is dried for 18 hours at 80° C. and under a pressure of 11 mm Hg. A white, crystalline product of the composition $\text{ZnX}_2$ (X=O-ethyl-α-(2-ethylhexylamino)-benzylphosphonate) is obtained in this way, and is readily soluble in toluene at room temperature and in hot ligroin. Its phosphorus content is 8.7% and its zinc content is 9.3%.

EXAMPLE 27

A solution of 20.7 g (0.1 mol) of 0-ethyl-α-morpholinomethanephosphonic acid in 500 ml of isoprepanol is treated, while hot, with a solution of 6.74 g (0.033 mol) of aluminium isopropylate in 900 ml of isopropanol. After boiling under reflux for one hour, the solvent is evaporated off and the residue is extracted with chloroform. After evaporating off the solvent, the extract is dried for 10 hours at 80° C. and under a pressure of 11 mm Hg. A pale beige coloured product of the composition $\text{AlX}_3$ (X=O-ethyl-α-morpholino-methanephosphonate) is obtained in this way, and is readily soluble in methylene chloride and in toluene at room temperature. Its phosphorus content is 13.7% and its aluminium content is 4.51%.

EXAMPLE 28

32.7 g (0.1 mol) of O-ethyl-α-(2-ethylhexylamino)-benzylphosphonic acid and 6.74 g (0.033 mol) of aluminium isopropylate are dissolved in 200 ml of benzene, the solution is boiled under reflux for one hour and the isopropanol formed is then distilled off. The solution is then clarified by filtration and is evaporated to dryness. The residue is dried for 10 hours over phosphorus pentoxide at 60° C. and under a pressure of 11 mm Hg. A strongly hydrophilic white product of the composition $\text{AlX}_3$ (X=O-ethyl-α-(2-ethyl-hexylamino)benzylphosphonate) is obtained in this way, and is readily soluble in all organic solvents at room temperature.

EXAMPLE 29

1,000 parts of polypropylene powder (melt index 1.5 g/10 minutes at 230° C., 2,160 g) are mixed in a drum mixer together with 1 part of pentaerythritol tetrakis [3-(3′,=′-di-tert. butyl-4-hydroxyphenyl)-propionate ] and 5 parts of a nickel compound from Table V which follows and the product is subsequently granulated in an extruder at a temperature of 200°-220° C.

The granules obtained are converted in the customary manner, by means of an extruder with a slit die, into a sheet, which is cut into tapes which are then stretched 5 to 6 times their length at elevated temperature and are wound up on a spool. The gauge of the tapes is 700–900 denier and their tensile strength is 5.5–6.5 g/denier.

The polypropylene tapes prepared in this way are placed on sample carriers without tension and are exposed in a 150 Xenotest apparatus. Groups of 5 samples are withdrawn after varying times and their tensile strength is determined. The "protection factor" which is defined as follows:

"Protection factor" = $\dfrac{\text{Time of exposure of the light-stabilised sample until it has lost 50\% of its tensile strength}}{\text{Time of exposure of the non-light-stabilised sample until it has lost 50\% of its tensile strength}}$ is used as a measure of the protective action of the individual nickel compounds.

The values obtained are listed in Table V which follows:

Table V

| Ni compound incorporated, according to Example | "Protection factor" | Time of exposure until 50% of the textile strength has been lost |
|---|---|---|
| None | 1.0 | 470 |
| 2 | 3.6 | 1700 |
| 3 | 1.7 | 790 |
| 4 | 4.0 | 1890 |
| 5 | 1.3 | 600 |
| 6 | 1.3 | 600 |
| 7 | 1.6 | 750 |
| 8 | 1.7 | 790 |
| 9 | 1.8 | 850 |
| 11 | 4.0 | 1890 |
| 14 | 4.1 | 1950 |
| 15 | 4.0 | 1890 |

Example 30

1000 parts of polypropylene powder [melt index 1.5 g/10 minutes (230° C., 2,160 g)] are mixed in a drum mixer together with 1 part of pentaerythritol tetrakis [3-(3',5'-di-tert.butyl-4'-hydroxyphenyl)-propionate], 5 parts of a metal complex and, in the case of formulation A, no further additive, and, in the case of formula B, with 3 parts of dilauryl thiodipropionate (DLTDP) and the product is then homogenised in a Brabender plastograph at 200° C. for 10 minutes. The metal complex used is designated in the first column of Table VI which follows.

The polymer composition obtained in this way is moulded in a heated press for 6 minutes, at the temperatures specified in the table, to give sheets 1 mm thick. A visual assessment of the discolouration of the samples gives the following results:

Table VI

| Metal complex incorporated, according to Example: | Color behaviour of the formulation | | | | | |
|---|---|---|---|---|---|---|
| | (without (DLTDP)) after 6 minutes at | | | B (with DLTDP) after 6 minutes at | | |
| | 260° C. | 280° C. | 300° C. | 260° C. | 280° C. | 300° C. |
| 1 | | n.d. | n.d. | n.d. | | |
| 2 | | n.d. | n.d. | n.d. | | |
| 3 | l.d. | | | | | |
| 4 | | | | n.d. | n.d. | n.d. |
| 5 | l.d. | | | | | |
| 8 | l.d. | | | | | |
| 11 | l.d. | | | | | |
| 16 | l.d. | l.d. | l.d. | n.d. | n.d. | n.d. |
| 21 | n.d. | n.d. | n.d. | n.d. | n.d. | n.d. |
| 23 | n.d. | n.d. | n.d. | n.d. | n.d. | n.d. |
| 25 | l.d. | l.d. | l.d. | l.d. | l.d. | l.d. |
| 26 | n.d. | n.d. | n.d. | n.d. | n.d. | n.d. |
| 28 | n.d. | n.d. | n.d. | n.d. | n.d. | n.d. |
| n-Butylamino complex of Ni(II)-2,2'-thio-bis-(p-di-tert.octyl-phenolate) | n.d. | d. | d. | n.d. | d. | d. |

Abbreviations: Degree of discolouration:
n.d. no discolouration
l.d. light discolouration
d. discoloured

What we claim is:

1. A compound of the formula

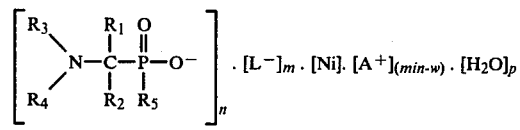

wherein $R_1$ and $R_2$ independently of one another represent hydrogen, alkyl, aralkyl, aryl or aryl wherein said or aralkyl which are substituted by chlorine and/or alkyl groups and/or alkoxy groups, or $R_1$ and $R_2$, conjointly with the C atom to which they are linked, form a cycloalkane ring, $R_3$ and $R_4$ independently of one another denote hydrogen, alkyl, alkoxyalkyl, cycloalkyl, aralkyl or aralkyl substituted by chlorine and/or alkyl groups and/or alkoxy groups, and, if none or only one of the substituents $R_1$ and $R_2$ represents an aromatic radical, $R_3$ and $R_4$ can also be aryl or an aryl radical substituted by chlorine and/or alkyl groups and/or alkoxy groups, $R_5$ denotes alkyl, cycloalkyl, aralkyl, aryl, alkoxy, cycloalkoxy, aralkoxy or aryloxy, or wherein the aromatic radical is substituted by chlorine and/or alkyl groups and/or alkoxy groups, $L^-$ denotes the monovalent anion of a carboxylic acid, $A^+$ denotes the cation of an alkali metal, n denotes an integer from 1 to 4, m denotes an integer from 1 to 3 or zero, w denotes an integer from 2 to 4, and p denotes a value from zero to 2, provided that, when m is zero the value of (m+n−w) is zero.

2. Compounds according to claim 1, characterised in that, $R_1$ and $R_2$ independently of one another represent hydrogen, alkyl having 1 to 12 C atoms, aralkyl having 7 to 11 C atoms, or aryl having 6 to 12 C atoms, or wherein the aromatic ring is monosubstituted or disubstituted by chlorine and/or methyl groups and/or alkoxy groups having 1 to 8 C atoms, or $R_1$ and $R_2$, conjointly with the C atom to which they are linked, form a cyclopentane or cyclohexane ring, $R_3$ and $R_4$ independently of one another denote hydrogen, alkyl having 1 to 12 C atoms, cycloalkyl having 5 or 6 C atoms, or an aralkyl radical which has 7 to 13 C atoms and which can be monosubstituted or disubstituted by chlorine and/or methyl groups and/or alkoxy groups having 1 to 8 C atoms, or, if none or only one of the substituents $R_1$ and $R_2$ represents an aromatic radical, $R_3$ or $R_4$ can also denote an aryl radical which can be monosubstituted or disubstituted by chlorine and/or alkyl groups having 1 to 4 C atoms and/or alkoxy groups having 1 to 8 C atoms, $R_5$ represents alkyl having 1 to 8 C atoms, cycloalkyl having 5 or 6 C atoms, aralkyl having 7 to 15 C atoms, or aryl having 6 to 12 C atoms, or wherein the aromatic ring is monosubstituted or disubstituted by chlorine and/or methyl groups and/or alkoxy groups having 1 to 8 C atoms, or $R_5$ denotes an alkoxy radical having 1 to 8 C atoms, the cyclohexexy radical, the benzoxy radical, the phenoxy radical or a phenoxy radical which is monosubstituted or disubstituted by chlorine or methyl groups, $L^-$ denotes the monovalent anion of an aliphatic carboxylic acid having 1 to 18 C atoms, or of cyclohexacarboxylic acid or of an aralphatic carboxylic acid having 8 to 12 C atoms or of an aromatic carboxylic acid which has 7 to 11 C atoms and which can be substituted by 1 to 2 alkyl radicals having 1 to 4 C atoms and/or by a hydroxy group, $M^{+w}$ represents a cation from the series of cations $Zn^{+2}$, $Al^{+3}$, $Co^{+2}$ or $Ni^2$, and n denotes an integer from 1 to 3, m denotes the number 1 or 2 or zero, and w denotes the number 2 or 3.

3. Compounds according to claim 2, wherein m denotes the number 1 or zero, n denotes the number 1 or 2, and w denotes the number 2.

4. Compounds according to claim 1, wherein $R_1$ and $R_2$ independently of one another denote hydrogen, alkyl having 1 to 8 C atoms, benzyl, phenyl or a phenyl radical substituted by a methyl or methoxy group, or wherein $R_1$ and $R_2$, conjointly with the C atom to which they are linked, form a cyclohexane ring, $R_3$ and $R_4$ independently of one another denote hydrogen, alkyl having 1 to 8 C atoms, cyclohexyl or an aralkyl radical which has 7 to 11 C atoms and which can be monosubstituted by methyl, chlorine or alkoxy groups having 1 to 4 C atoms, or, if none or only one of the substituents $R_1$ and $R_2$ represents an aromatic radical, $R_3$ or $R_4$ can also denote a phenyl radical which can be monosubstituted or disubstituted by chlorine and/or alkyl groups having 1 to 4 C atoms and/or alkoxy groups having 1 to 4 C atoms, $R_5$ denotes alkyl having 1 to 8 C atoms, cyclohexyl, aralkyl having 7 to 11 C atoms, an aryl radical which has 6 to 10 C atoms and which can be monosubstituted by Cl, $CH_3$ or $CH_3O$, an alkoxy radical having 1 to 4 C atoms, the benzoxy radical, the phenoxy radical, a chlorophenoxy radical or a tolyloxy radical, $L^-$ represents the anion of acetic acid, 2-ethylcaproic acid, lauric acid, oleic acid, stearic acid, phenylacetic acid, benzoic acid, 4-hdyroxy-3,5-di-tert-.butylbenzoic acid or naphthoic acid, n denotes an integer from 1 to 3, m denotes the number 1 or 2 or zero, and w denotes the number 2 or 3.

5. Compounds according to claim 4, wherein n is the number 1 or 2, m is the number 1 or zero, and w is the number 2.

6. Compounds according to claim 1, wherein $R_1$ denotes hydrogen, alkyl having 1 to 6 C atoms, phenyl or 4-methoxyphenyl, $R_2$ denotes hydrogen or methyl, $R_3$ denotes hydrogen, alkyl having 2 to 8 C atoms, cyclohexyl or benzyl, $R_4$ denotes hydrogen, alkyl having 2 to 8 C atoms, cyclohexyl, phenyl, 4-methoxyphenyl or 2-methoxy-5-tert.butylphenyl, $R_5$ denotes alkyl having 1 to 4 C atoms, phenyl, 4-tolyl, 4-methoxyphenyl or an alkoxy radical having 1 to 4 C atoms, $L^-$ denotes the anion of acetic acid, 2-ethylcaproic acid, lauric acid, stearic acid or 4-hydroxy-3,5-di-tert.butylbenzoic acid, $A^+$ denotes the cation $Na^+$ or $K^+$, n denotes the number 1 or 2, m denotes the number 1 or 2 or zero, and w denotes the number 2.

7. The compound of claim 1 of the formula
$[(C_2H_5)_2N-CH_2-P(O)(OC_4H_9)O]_2Ni \cdot H_2O$.

8. The compound of claim 1 of the formula

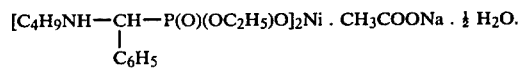

9. The compound of claim 1 of the formula

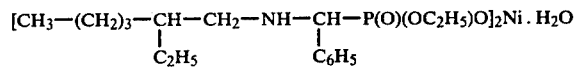

10. The compound of claim 1 of the formula

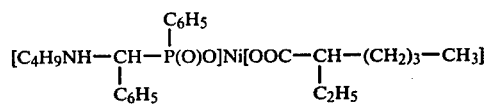

11. A composition stabilized against UV light degradation comprising a polymeric material normally subject to UV light degradation and from 0.01 to 5% by weight of a compound according to claim 1.

12. A composition stabilized against UV light degradation comprising a polymer material normality subject to UV light degradation and from 0.0125% by weight of a compound according to any one of claim 1.

13. Composition of matter according to claim 11, characterised in that the polymer is a polyolefine.

14. Composition of matter according to claim 13, characterized in that the polymer is polypropylene or propylene copolymer selected from the group consisting of ethylene, propylene, propylene-butene-1, and ethylene-propylene-diene.

* * * * *